United States Patent [19]
Hill et al.

[11] Patent Number: 5,741,980
[45] Date of Patent: Apr. 21, 1998

[54] FLOW ANALYSIS SYSTEM AND METHOD

[75] Inventors: Wayne S. Hill, Westborough; Bruce N. Barck, Franklin, both of Mass.

[73] Assignee: Foster-Miller, Inc., Waltham, Mass.

[21] Appl. No.: 784,787

[22] Filed: Jan. 16, 1997

Related U.S. Application Data

[63] Continuation-in-part of Ser. No. 333,213, Nov. 2, 1994, Pat. No. 5,600,073.
[51] Int. Cl.$^6$ ................................................. G01F 1/74
[52] U.S. Cl. ........................................................ 73/861.04
[58] Field of Search ........................... 73/861.04, 29.01, 73/23.2, 24.01, 659, 30.03

[56] References Cited

U.S. PATENT DOCUMENTS

| | | | |
|---|---|---|---|
| H608 | 3/1989 | Goolsby | 367/89 |
| 3,392,572 | 7/1968 | Brown | 73/29.01 |
| 4,576,036 | 3/1986 | Huang et al. | 73/29.01 |
| 4,688,418 | 8/1987 | Cheunh et al. | 73/29.01 |
| 5,390,547 | 2/1995 | Liu | 73/861.04 |
| 5,419,197 | 5/1995 | Ogi et al. | 73/659 |
| 5,600,073 | 2/1997 | Hill | 73/861.04 |

Primary Examiner—Richard Chilcot
Assistant Examiner—Jewel Artis
Attorney, Agent, or Firm—Iandiorio & Teska

[57] ABSTRACT

A non-invasive flow analysis system and method wherein a sensor, such as an acoustic sensor, is coupled to a conduit for transmitting a signal which varies depending on the characteristics of the flow in the conduit. The signal is amplified and there is a filter, responsive to the sensor signal, and tuned to pass a narrow band of frequencies proximate the resonant frequency of the sensor. A demodulator generates an amplitude envelope of the filtered signal and a number of flow indicator quantities are calculated based on variations in amplitude of the amplitude envelope. A neural network, or its equivalent, is then used to determine the flow rate of the flow in the conduit based on the flow indicator quantities.

50 Claims, 5 Drawing Sheets

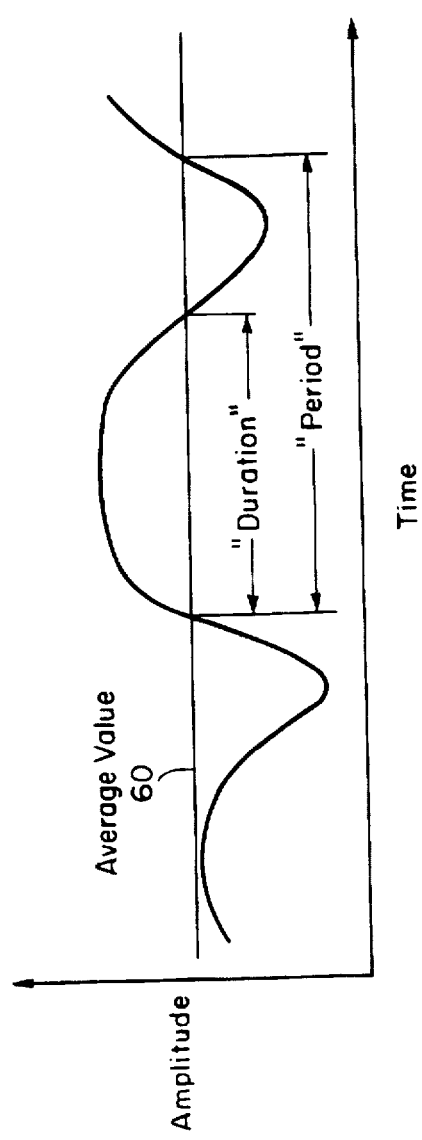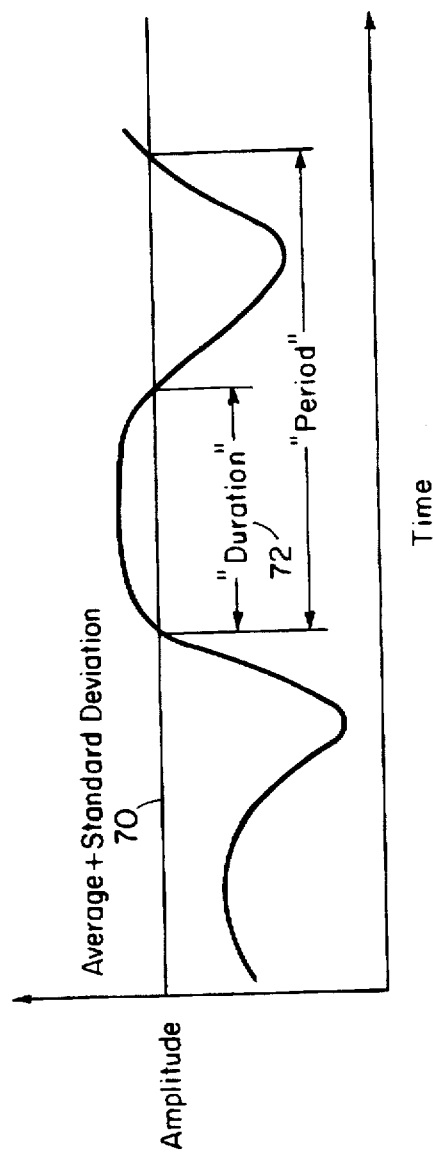

FLOW ANALYSIS SYSTEM AND METHOD

RELATED INVENTIONS

This application is a continuation-in-part application of U.S. patent application Ser. No. 08/333,213, filed Nov. 2, 1994, U.S. Pat. No. 5,600,073.

GOVERNMENT RIGHTS

This material is based upon work supported by NASA Contract Number NAS-13-691. The Government, therefore, has certain rights in this invention.

FIELD OF INVENTION

This invention relates to a method and system for analyzing different types of flows in a conduit including single or two phase flows and for determining the mass flow of a single phase flow or quality and mass flow rate of a two phase flow using non-invasive sensors.

BACKGROUND OF INVENTION

A two phase flow in a conduit is a flow which includes both gas and liquid, or gas and solid, or liquid and solid. An example of a gas/liquid two phase flow is water and air flowing in a pipe; an example of a gas/solid two phase flow is coal particles and air flowing in a pipe. Ultrasonic methods for determining the presence of a two phase flow in a conduit are known. See, e.g., US statutory invention registration No. H608. Essentially, an ultrasonic pulse is sent transversely through a pipe and if the flow is single phase (i.e. all liquid), a return pulse is detected after a time lag as a return echo which is strong and reasonably sharp off the far wall of the pipe. If gas bubbles are entrained in the liquid, there are multiple small reflections and diffusion or attenuation of the main return echo off the far wall of the pipe. If a two phase flow with a defined gas/liquid interface is present in the pipe, the return echo is fairly strong but earlier in time than in the situation where there is only liquid flow since the return echo bounces off the gas/liquid interface instead of the far wall of the pipe. Finally, if the flow has a defined gas/liquid interface and also gas bubbles in the liquid, there are multiple small reflections due to the bubbles in the liquid and the return echo is both attenuated and earlier in time than would be the case with only liquid flow. Such measurement methods, however, which only detect the presence of a two-phase flow, do not completely define the two phase flow.

Quality is the mass fraction of the two-phase flow that is in the gaseous phase. Quality together with mass-flow determines the amount of energy (enthalpy) that is convected by the flow and thus is a key variable used to define the status of the flow system. Accordingly, quality and/or mass flow measurements are needed to fully define the flow. One reason that mass flow rate and the quality measurements are needed is to adjust the rate of one phase of the flow in a system.

A typical liquid/gas two phase flow comprises a liquid film in contact with part or all of the conduit wall (depending on flow parameters and flow orientation with respect to gravity). The liquid is largely separate from a continuous or intermittent vapor flow. Since an identifiable liquid-vapor interface exists, it is possible to analyze the geometry, flow rate, and axial pressure drop behavior of the liquid and vapor flow separately, equating boundary conditions as appropriate. If the thickness of the liquid flow in the conduit can be determined, various flow models can be used to predict fill thickness versus quality for a number of mass flow rates. See, for example, Wallis, G. B., *One-dimensional Two-Phase Flow*, McGraw-Hill, New York, N.Y., 1969, pages 51–54, and 315–374; Lockhart, R. W. and Martinelli, R. W. "Proposed Correlation of Data for Isothermal Two Phase, Two Components Flow in Pipes", Chemical Engineering Progress, Volume 45, No. 1, 1949, pages 39–48; and Deissler, R. G., "Heat Transfer and Fluid Friction for Fully Developed Turbulent Flow of Air and Super Critical Water with Variable Fluid Properties", Transactions, ASME volume 76, No. 1, 1954, page 73.

But the precursor step of detecting the thickness of the liquid flow using ultrasonic methods is troublesome. The presence of bubbles of gas in the liquid flow, the presence of large waves of liquid traveling in the conduit, small scale thickness changes in the liquid/vapor interface, and other similar "chaotic" conditions within the conduit severely affect the ability to determine fill thickness using ultrasonic techniques. If one or more of these conditions are present within the conduit, a plot of the return echoes from an ultrasonic transducer is not a good indicator of film thickness. Moreover, a low flow rate with a high quality results in a highly chaotic flow as does a high flow rate with a low quality. Such chaotic flows render known film thickness measurement techniques unreliable.

Therefore, a trace of the return echoes from such a chaotic flow alone is seemingly not a good indicator of film thickness. Other techniques for measuring the thickness of the liquid film that is usually in contact with the wall of the conduit include sampling, thermal probes, film conductivity or capacitance measurements, and gamma densitometry. Although each of these techniques exhibits strengths and weaknesses, no technique offers the advantages of reflective-mode ultrasound. Ultrasound techniques are non-invasive, offer rapid response, excellent long term accuracy and sensitivity, and are applicable to all working fluids over a very broad range of temperatures. Moreover, even if non-ultrasonic thickness measurement techniques are used, the various flow models used to evaluate flow quality and mass flow rates are based on a number of assumptions which can lead to inaccuracies. On the other hand, quality and/or mass flow measurements cannot be accurately taken without measuring film thickness or a related parameter, void fraction. Flow meters, for example, do not indicate how much of the flow is liquid or gas and flow meters cannot be used in all situations.

A typical gas/solid two phase flow, such as coal particles entrained in an air flow, generally comprises a rope like structure of coal particles travelling in the pipe. There are no current techniques which accurately measure the mount of coal in the pipe. Trial and error methods commonly used in coal power plant operation, can result in poor efficiency and air pollution. In order to optimize combustion, the amount of coal and the amount of air delivered to the burner must be known.

Therefore, in addition to determining the presence of a two phase flow, considerable research has been performed on various means of actually measuring two-phase flows. These efforts have largely attempted to characterize an average value of some aspect of the flow, such as a pressure drop, void fraction, fill thickness, velocity, or density. One problem with this approach is that knowledge of any single value is not sufficient to define a two-phase flow. Two-phase flows comprise two separate flows (of phase A and Phase B) that interact in extremely complex ways. If average values are used, at least two independent quantities must be measured to define the flow. In addition, a given pair of observations, such as a pressure drop and a velocity, often does not provide a sensitive indication of the flow rates of phase A and phase B for a broad range of conditions. Thus, different combinations of observations are often needed for different flow conditions.

There are applications that can be well served by suitably developed instruments based on currently known averaging techniques. However, there are many more applications for which combinations of currently available averaging measurements will not provide desirable results. For example, some applications demand a completely non-invasive flow measurement. Others may be geometrically constrained, so that only instruments of a given size or shape may be used. Other applications may require accurate flow measurement over an extremely broad range of flow conditions. Still others may be very cost-driven, so that the instrument must be very inexpensive. The current invention offers the advantage that any meaningful measurement technique, used rapidly and persistently, can be used to determine the flows of both phases. Since every application permits at least some meaningful flow observation to be made, the current invention ensures that a practical instrument can be developed.

The approach of the subject invention arises from simple, but profound observations about two-phase flows. First, they are deterministic, in that they satisfy the laws of physics. Thus, while their evolution is extremely complex, there is an underlying order to the flow behaviors. The behavior of a given wave, particle, or bubble, although complicated, is not truly random.

Second, since they are deterministic and behave in a complex fashion, they are likely to be chaotic. The word "likely" is used here because it has not yet been proven in generality that fluid turbulence satisfies the mathematical definition of chaos. It is not yet known what (if any) kinds of complex behaviors are possible that are neither chaotic nor random. It currently is not possible to make generalities about the behaviors of such a system. For want of a more conclusive answer from topologists, and since the view of two-phase flows as chaotic is consistent with the evidence so far available, the current invention assumed that the two-phase flows of interest are chaotic.

Two-phase flows are dissipative, i.e. given the opportunity, any work that is imposed on them is eventually lost to viscosity. Thus, given an arbitrary initial condition (e.g., means of mixing at the inlet to the flow conduit), a two-phase flow will settle into a pattern of behavior that is similar to that of other flows with the same flows of phase A and phase B but different initial conditions. Actually, it is difficult to prove this conclusively without generating many flow conditions with a variety of initial conditions and comparing their properties in detail. However, it is a basic tenet of the arts of fluid mechanics and two-phase flow that this is the case: if this were not the case, it would not be possible to generate models or correlations of two-phase flow behaviors. This is also consistent with the properties of dissipative chaotic systems.

If two-phase flows are dissipative and chaotic, then key statements can be made about their behaviors. Principal among these is the existence of a single underlying behavior, a "strange attractor", the shape of which changes as flow parameters change. The strange attractor is an extremely complicated path (in mathematical phase space) that defines all trajectories of the system with time. It is limited to a finite portion of phase space and is a single unending, open (i.e., never repeating) path in which points that are initially near one another diverge rapidly from one another with time (called sensitivity to initial conditions). The conclusions that can be drawn from the existence of a strange attractor are far-reaching. The principal conclusion for current purposes is that any observation of the system behavior, made over a period of time, is a mapping of the strange attractor. If the observation is made with constant time increment between measurements, it is a smooth mapping. Any smooth mapping of a strange attractor contains an mount of information about the system behavior that is comparable to any other smooth mapping with the same time increment and measurement sensitivity. Thus, any of a variety of measurement methods may be used with a two-phase flow with equal conviction that meaningful information is obtained.

This line of discussion is fairly well established in the art of chaos theory, but by itself is not sufficient to permit the measurement of two-phase flows. The reason for this is that the argument does not disclose how the evolution of the flow observations can be related to the flow conditions. In fact, various researchers have attempted to relate two-phase flow conditions to time-series measurement. The best known of these are Jones, O. C. and Zuber, N., "The Interrelation between void fraction fluctuations and flow patterns in two-phase flow" Int'l J. of Multiphase Flow, v2, page 273–306, 1975; Hubbard, M G., and Dukler, A. E., "The Characterization of Flow regimes for Horizontal two-phase flow: 1. statistical analysis of wall pressure fluctuations", Proceedings of the 1966 Heat Transfer and Fluid Mechanics Institute, Saad, M. A. and Miller, J. A. eds., Standard University Press, pages 100–121, 1966. Jones and Zuber identified liquid-gas flow regimes from the probability density function of X-ray attenuation measurements. Hubbard and Dukler identified flow regimes from frequency spectra of pressure signals from liquid-gas two-phase flows. In neither of these cases was the flow rate of either or both phases determined.

The technical literature has many references describing efforts to examine or develop instruments of various kinds to measure or characterize two-phase flows. Overviews include Hsu, Y. Y., and Graham, R. W., Chapter 12: Instrumentation for Two-Phase Flow, in *Transport Processes in Boiling and Two-Phase Systems*, McGraw-Hill, 1976; and Mayinger, F., Chapter 16: Advanced Optical Instrumentation, in *Two-Phase Flow and Heat Transfer in the Power and Process Industries*, Bergles, A. E., et al, editors, Hemisphere Publishing Company, 1981. The bulk of these efforts have generated results of sufficiently limited application to have remained largely of research interest. True two-phase flowmeters, i.e., instruments that purport to define the flows of both phases A and B, are not widely available on the commercial market.

In industrial practice, the most widely used instruments for two-phase flows have been photon attenuation instruments. These instruments determine the attenuation of photons (typically microwaves or gamma rays) as they pass through the flow. The greater attenuation of one phase than the other (essentially from higher density) is used to characterize the portion of the flow channel cross section that is filled with each phase. Alternatively, this may be viewed as characterizing the average density of the flow. Depending upon the specific geometry of the instrument, it may be rendered more or less sensitive or the distribution of the phases across the flow channel, and thus may be used to identify the flow regime (e.g., bubbly, slug, stratified, annular, or mist flows). These instruments provide only a rough indication of the flow condition, because their sensitivity to the amount of each phase that is present is limited. In particular, gamma densitometers are highly sensitive to even trace quantities of lead in a flow, severely limiting their accuracy in many applications of interest (most notably in petroleum pipelines). Despite the limitations of these instruments in their originally intended embodiment, they could be used to advantage with the current invention to accurately determine the flows of phases A and B.

To generate useful information about the flow rates of phases A and B, an attenuation measurement must be combined with some indication of flow velocity. Such an indication may be obtained by making attenuation measurements at two closely spaced stations along the flow duct and cross-correlating the resulting signals. The time delay of the peak in the cross-correlation curve corresponds to an approximate time delay for flow propagation. Dividing the spacing of the instruments by this time delay provides a characteristic velocity. The average flow density and this velocity can be correlated to the flow rates of phases A and B. Correlation is needed to correct for the inevitable "slip" that occurs between phases (because they do not flow with identical velocity).

Even with suitable calibration, the accuracy of cross-correlated attenuation measurements is limited because of the poor sensitivity of the density measurement for many flow conditions. This limited accuracy is implied in U.S. Pat. No. 4,683,759 to Skarvaag et al, wherein, this basic idea is used to measure liquid-gas two-phase flows. However, the determination of liquid and gas flow rates is discussed for only one specific flow regime, called slug flow, in which the liquid and gas flows are largely intermittent, and the peak in the cross-correlation function quite sharp.

Other instrument systems have been devised to observe two-phase flows. In U.S. Invention registration H608 to Goolsby, an ultrasonic measurement technique is used to determine whether gas is present in a liquid flow. In this instrument, echo-mode ultrasound is used to determine the location of the second major reflection interface (the first being between the liquid and the tube wall). If the time-off-flight of the acoustic wave is less than that associated with a full tube (second reflection from the far wall), then a liquid-gas interface is present. Actually, this approach has been used to study two-phase flows quantitatively for quite a few years.

In U.S. Pat. No. 4,193,291 to Lynnworth, an ultrasonic method of determining flow density is described. This technique is based on the different attenuation rates of torsion waves in a body depending upon the density of the fluid in which the body is immersed. Various embodiments are described that render the instrument more or less sensitive to the distribution of the phases in the flow duct. This instrument is limited to liquid—liquid or liquid-gas two-phase flows. One unfortunate aspect of this instrument is its intrusiveness into the flow. The protrusion of the instrument into the flow raises the potential for damage to the instrument from debris carried by the flow, generates an undesirable pressure drop and flow disruption, and requires seals between the instrument and the flow duct which reduce the reliability of the flow system. Another unfortunate aspect of this instrument is that no single embodiment is described that determines the average density across the entire flow cross section. Thus, each embodiment is applicable to a limited range of flow regimes. Further, the issue of fluid wetting is not addressed: if the liquid wets the material of the sensor, the apparent density may be skewed strongly toward the liquid density. Even with these limitations, the mechanism of this measurement approach could be used with the current invention to provide an accurate determination of the flow rates of phases A and B.

The aforementioned patent states that the density measurement may be combined with acoustic velocimetry to determine the flow rates of both phases. In acoustic velocimetry, an acoustic wave is propagated by one transducer downstream through the flow and its time-of-flight to another transducer measured. A second wave is propagated upstream to determine the propagation time against the flow. Comparison of these propagation times determines both the effective speed of sound of the flow and its propagation velocity. If acoustic velocimetry works in two-phase flows at all, the measurements would be very sensitive to the flow regime. For example, in annular flow, a continuous liquid film is in contact with the flow duct wall. Any acoustic waves that enter the flow will effectively "short circuit" through the liquid (with its very high sonic velocity and relatively low attenuation) so that only the liquid velocity (skewed by the acoustic wave path) would be measured. By contrast, in stratified flow, a liquid flow on the bottom of the flow duct is effectively separated from a gas flow in the top of the duct. If acoustic waves traveling through the liquid can couple sufficiently with the gas flow, then a velocity that is an average of the liquid and gas velocities will be measured. This velocity would be quite different from (much higher than) that of an annular flow, even though annular flows often occur at much higher velocities. Thus, the calibration of the instrument output with different flow conditions would involve some very strong nonlinearities likely to result in poor accuracy.

U.S. Pat. No. 4,991,124 to Kline describes a different ultrasonic instrument for determining a fluid density. This technique is based on determining the velocity of sound and rate of attenuation of acoustic energy in the fluid. Because this technique relies on multiple reflections of the acoustic energy, which would be extremely difficult to detect in two-phase flows, it probably could not be applied to a two-phase flow.

AEA Technology, of the United Kingdom, has publicized a two-phase flowmeter for use in oil and gas fields [Anonymous, "Non-Intrusive Meter Measures Oil and Gas Flows", Competitive Edge, Issue 4, pg. 3, Spring, 1994]. This instrument uses a pulsed neutron beam which counts hydrogen, carbon, oxygen, and chlorine atoms passing the sensing point. Short bursts of radiation are used to activate oxygen atoms, which can be tracked as they move to define a flow velocity (a second measurement method). This instrument employs two averaging techniques to determine the flow rates of (potentially) several phases. However, it depends upon the phases being of distinct compositions to define their flow rates separately. If the two phases were of the same composition (a so-called single-component two-phase flow), then only a total flow measurement would be obtained. While this system may prove effective for its intended application in oil fields, its cost, complexity, and operational limitations will limit its use elsewhere.

Finally, the analysis of liquid and two-phase flows of cryogenic propellants presents a number of unique problems. The fact that the flow is unavoidably two-phase during start up and in certain transients is one major problem. Intrusive mechanical flow meters can not accurately analyze two-phase flows. Turbine meter moving parts can be destroyed, and even orifice plates and venturies can suffer significant erosion. These problems are particularly severe in the case of liquid oxygen flows which can rapidly destroy welded components. Intrusive flow measurement devices also require the minimization of the pressure drop and can, in some situations, cause a severe hazard. For example, coriolis mass flow meters are notoriously unreliable with two-phase flows. See Baird, R. S., "Flow Meter Evaluation For On-Orbit Operations," NASA technical memorandum 100465, August 1988. Magnetic flow meters do not work with conductive fluids or two-phase flows. Also, past efforts to use triboelectric measurements have also proven to be unsatisfactory. See Bernatowicz, H.; Cunningham, J. and Wolff, S., "Mass Flow Meter Using The Triboelectric Effect For Measurement In Cryogenics," NASA CR-179572, April 1987; and Dechene, R., "Mass Flow Measurement Of Liquid Cryogens Using The Triboelectric Effect," NASA CR-179519, August 1986. One current effort to use active ultrasonic measurements suffers the limitation of signal loss during the inverted angular flow transient that is common with system start-up, and the loss of accuracy with the significant gaseous void fraction.

Accordingly, measurement of liquid and two-phase flows of cryogenic propellants and other fluids in the oil and gas industry, the chemical processing industry, and the nuclear and fossil fuel power generation industry requires a non-intrusive sensor, operable at temperatures ranging from the cryogenic level to high levels which provides a reliable measurement of both liquid and two-phase flows.

Unfortunately, no such system exists at the present time.

SUMMARY OF INVENTION

It is therefore an object of this invention to provide a highly reliable and efficient flow analysis system and method.

It is a further object of this invention to provide such a flow analysis system and method which is non-intrusive.

It is a further object of this invention to provide such a flow analysis system and method which is capable of operating at cryogenic or elevated temperatures and in adverse conditions.

It is a further object of this invention to provide such a flow analysis system and method which provides reliable measurement of both liquid and two-phase flows.

This invention results from the realization that the flow rate, the flow quality, and other flow parameters of a single phase or a two phase flow in a conduit can be accurately and efficiently determined by using a passive sensor such as an acoustic sensor or a strain gauge type transducer, filtering the sensor output to pass only the resonant behavior of the sensor, capturing the amplitude envelope of the filtered signal, sampling the amplitude envelope, calculating a number of flow indicator quantities based on variations in the amplitude of the signal, and using a trained neural network to characterize the flow based on the flow indicator quantities.

This invention features a flow analysis system and method. The system includes a sensor in communication with a conduit which has a flow therein. The sensor transmits a signal which varies depending on the characteristics of the flow in the conduit. There is a filter, responsive to the sensor signal, and tuned to pass a narrow band of frequencies proximate to the resonant frequency of the sensor. There are means for generating an amplitude envelope representative of the sensor signal, and there are also means, responsive to the amplitude envelope, for calculating a plurality of flow indicator quantities representative of the flow in the conduit. Such means may include the computer program included herein. Finally, there are means, responsive to the flow indicator quantities, for determining the flow rate of the flow in the conduit. Preferably, such means include a trained neural network which receives the flow indicator quantities as input and outputs, for example, the liquid flow rate and the gas flow rate of a two-phase flow in a conduit.

The means for calculating preferably includes means for sampling the amplitude envelope at a rate less than or equal to the resonant frequency of the sensor to efficiently analyze the sensor signal. Typically, variations in the amplitude of the amplitude envelope are used to calculate the flow indicator quantities. One such flow indicator quantity includes the average value of the amplitude of the amplitude envelope. Another flow indicator quantity includes the standard deviation of the amplitude. Still another flow indicator quantity includes the characteristic auto-correlation time of the amplitude envelope. Numerous other flow indicator quantities are calculated based on variations in the amplitude of the sensor signal. In a preferred embodiment, the sensor is an acoustic sensor.

This invention also features a flow analysis method. A sensor is coupled to a conduit in order to transmit a signal which varies depending on the characteristics of the flow in the conduit. A filter, responsive to the signal and tuned to pass a narrow band of frequencies proximate the resonant frequency of the sensor, is used. This filtered signal is demodulated and amplified and used to calculate a plurality of flow indicator quantities representative of the flow in the conduit. The flow rate of the flow in the conduit is then determined using the flow indicator quantities.

DISCLOSURE OF PREFERRED EMBODIMENT

Other objects, features and advantages will occur to those skilled in the art from the following description of a preferred embodiment and the accompanying drawings, in which:

FIG. 6 is a graph depicting one particular flow indicator quantity used to characterize a flow in accordance with the subject invention;

FIG. 7 is a graph depicting another flow indicator quantity used to characterize a flow in accordance with the subject invention.

Figure 1:
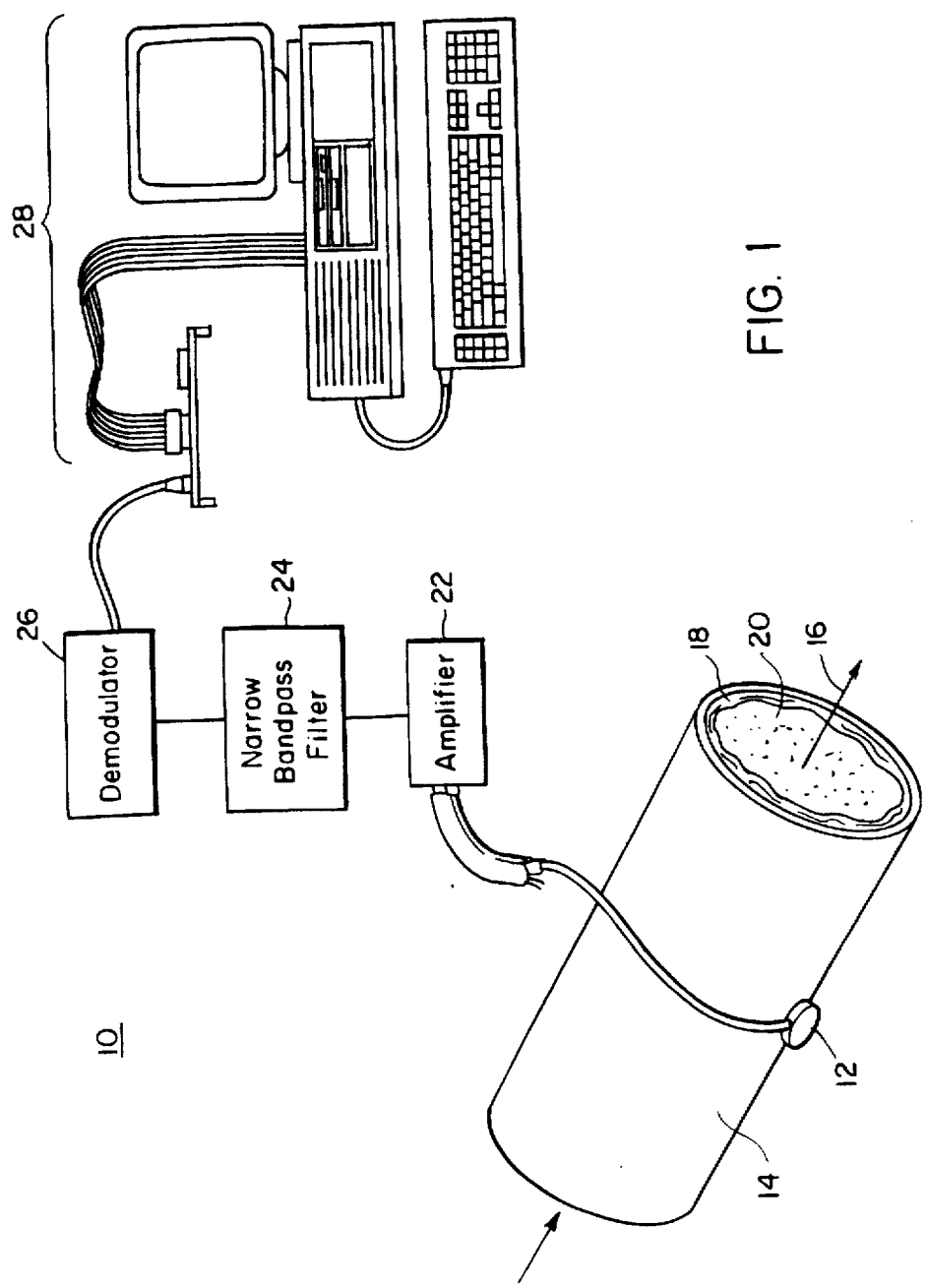
FIG. 1 is a schematic view of the flow analysis of this invention.

Flow analysis system 10, FIG. 1, includes sensor 12 attached to conduit 14 which includes a flow therein in the direction of vector 16. In FIG. 1, the flow is shown as a two-phase flow with liquid 18 and gas 20 components although this is not a necessary limitation of the subject invention. Sensor 12 is preferably a passive acoustic "ClampOn 2000 Particle Monitor" available from ClampOn AS of Norway. As an alternative, an Endevco Model 7259A accelerometer may be used. The voltage signal from sensor 12, which varies as a function of the condition of the flow in conduit 14, is sent to amplifier 22 and then passed to narrow band pass filter 24 which is preferably tuned to pass a narrow band of frequencies proximate the resonant frequency of the sensor (e.g., approximately 83 kHz for the "ClampOn" sensor; approximately 93 kHz for the Endevco sensor). Also included within flow analysis system 10 are some means for generating an amplitude envelope of the filtered signal, for example, demodulator 26. A demodulator circuit such as a Signetics ULN2209 and MC1496K integrated circuits may be used. In response to the demodulated signal, computer subsystem 28 digitizes the demodulated, filtered, and amplified signal and calculates a plurality of flow indicator quantities representative of the flow in the conduit. Computer sub-system 28 includes a 16 bit data acquisition board capable of 100 kHz sampling. There are also some means, responsive to the flow indicator quantities, for determining the flow rate of the flow in the conduit. In a preferred embodiment, such means include a trained neural network discussed below with reference to FIG. 8.

"ClampOn" sensor 12 has a resonant frequency of approximately 83 kHz. Its passive nature, with no power dissipated at the sensor location, and its piezoelectric operating principle, offers both ruggedness and capability of operation in a very broad range of temperatures and is thus ideal for cryogenic applications. Sensor 12 produces a very low level voltage output in response to turbulence-induced acoustic events that occur in the flow as it passes by. Because filter 24 discards all behaviors that do not excite the transient resonant response of sensor 12, the output of filter 24 is fairly insensitive to structure-born mechanical vibration and audible noise. Other sensors, however, such as the ultrasonic sensor shown in the parent application incorporated herein by this reference, may also be used.

Figure 2:
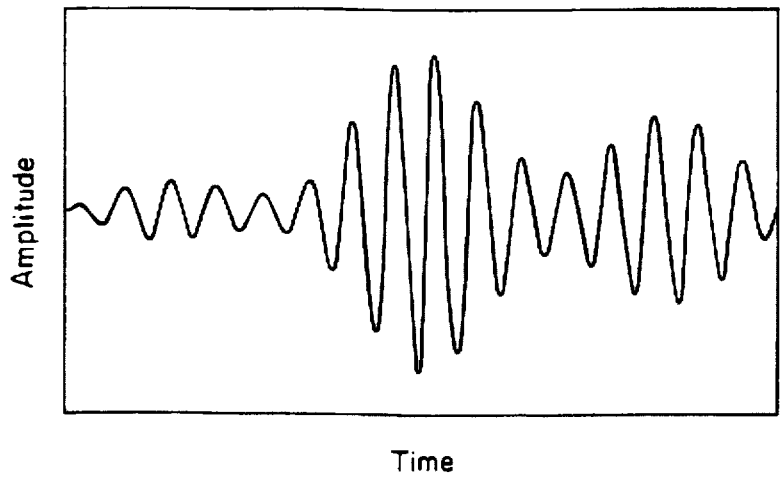
FIG. 2 is a graph depicting the variation in the amplitude of the sensor signal generated by the flow analysis system shown in FIG. 1.

High gain amplifier 22 boosts the low level output of the sensor to a voltage level signal useful for data acquisition purposes. Narrow band pass filter 24 is centered around the natural frequency of sensor 12. Thus, the voltage signal provided to demodulator 26 also has a frequency of 83 kHz as shown in FIG. 2. The reason for narrow band pass filter 24 is as follows. Any linear mechanical element (such as acoustic sensor 12) has two responses to a periodic driving force: a steady-state solution at the frequency of the driving force and a transient solution at the resonant frequency of the mechanical element. The response to any combination of driving forces can be viewed as a sum of these behaviors. In a flow situation, the driving forces of interest are inherently transient, because they involve acoustic events resulting from passage of turbulence induced flow fluctuations. Thus, the principal flow information is almost certainly contained in the part of this signal that occurs at the resonant frequency. Spurious effects, whether from electromagnetic interference, amplifier noise, external mechanical noise, and the like occur over a broad range of frequencies. These behaviors, which are likely to be confusing to the analysis, are largely ignored by the use of band pass filter 24.

Figure 3:
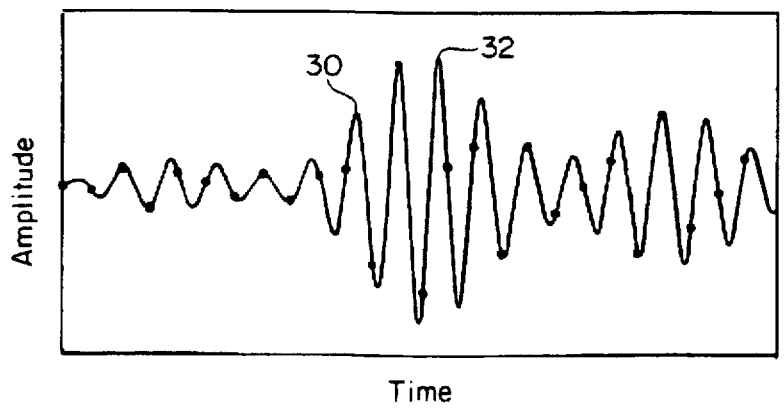
FIG. 3 is a graph showing a sampling rate of 100 kHz of the signal shown in FIG. 2.

The reason for demodulator 26 is explained as follows. The sensor signal at the output of band pass filter 24 has a varying amplitude and a very narrow frequency range centered about 83 kHz. Thus, a sampling rate of at least 252 kHz representing four samples per period would be needed to characterize the variation in amplitude accurately. Sampling at a more reasonable rate, for example 100 kHz, would only obtain approximately 1.2 samples per period as shown in FIG. 3 wherein the black dots represent samples. As shown in FIG. 3, any sampling rate of less than 252 kHz would not capture all of the signals character. Note that the amplitude rise as shown at 30 would be missed as would the amplitude rise shown at 32.

The subject invention includes means for calculating a variety of statistics that characterize different behaviors of the time variation of the signal shown in FIGS. 2 and 3. A few of these "flow indicator quantities" are fairly straight forward. Examples include the signal's average value or its standard deviation. Other flow indicator quantities, however, are more involved and are intended to quantify the specific aspects of the signal such as the characteristic sizes, durations, or sequences of behaviors in the signal dynamics. Any sampling rate which misses the amplitude rises as shown at 30 and 32 could result in erroneous readings.

A sampling rate of 252 kHz would correctly sample the amplitude rises at 30 and 32. Such a high sampling rate however, would require an extremely sophisticated data acquisition processing system. Same is true for a sampling rate of even 100 kHz.

Figure 4:
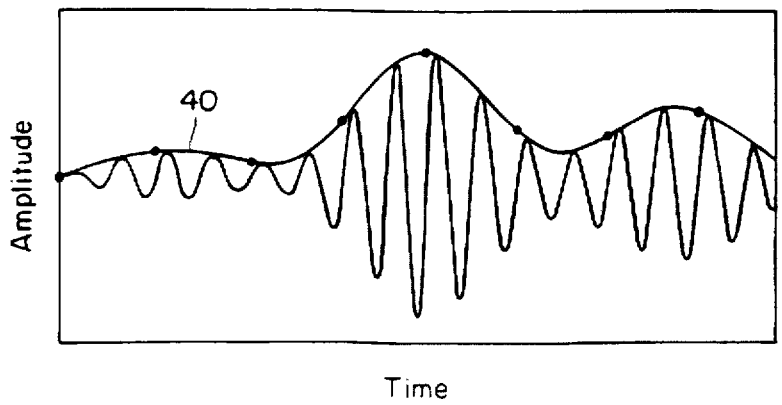
FIG. 4 is a graph showing the demodulated signal of FIG. 2 and a much lower and more efficient sampling rate.

Accordingly, in the subject invention, demodulator 26 is used to generate signal envelope 40, FIG. 4, which contains all of the key information about the sinusoidal variations of the sensor signal. Accordingly, a much lower sampling rate can then be used to fully characterize the signal variation. Thus, in the subject invention, even a 30 kHz sampling rate can be used to capture the complete character of the signal. This lower sampling rate is far easier to achieve in real time than the higher rates required to fully capture the detail dynamics of a 83 kHz signal.

Figure 5:
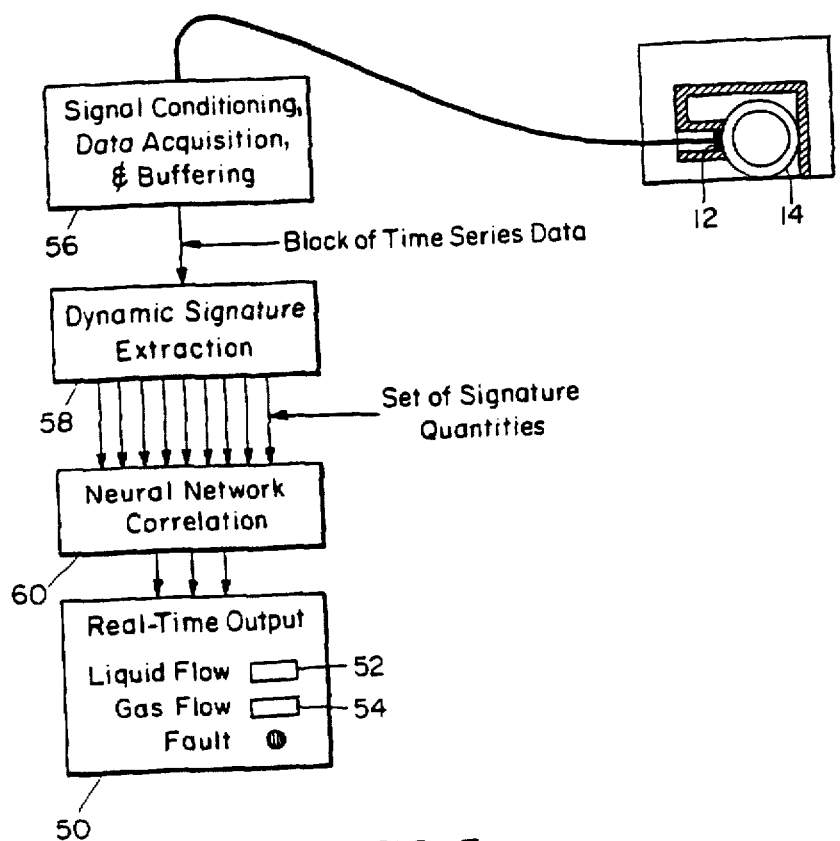
FIG. 5 is a block diagram of the primary components of the flow analysis system of this invention.

In this invention, then, a liquid flow rate of a two-phase flow is displayed via monitor 50, FIG. 5, at 52 and the gas flow rate as shown at 54 may be provided in real time. "ClampOn" sensor 12 is clamped to conduit 14 and the resulting signal is sent to signal conditioning, data acquisition, and buffering electronics 56 which include amplifier 22, narrow band pass filter 34, and demodulator 26, FIG. 1. Computer software, described in more detail below, operating on computer sub-system 28, FIG. 1, receives the resulting signal, digitizes it, and calculates a plurality of flow indicator quantities schematically shown in block 58, FIG. 5. These flow indicator quantities are then presented to the neural network correlation sub-system 60, also operating on computer sub-system 28, FIG. 1 to provide real time output to monitor 50, FIG. 5.

Two seconds or more of data for each test condition may be collected resulting in 200,000 readings in each data file. Such a data collection is best for measuring flows of pure liquid, where the dynamics are driven by small scale turbulent eddies. Two-phase flow conditions often require a longer observation period because they are characterized by the passage of longer events such as slugs or waves of fluid. Stored in ASCII format, each file would consume approximately 1.5 MB of disk space. In 241 tests, over 350 MB of raw data is collected.

One such flow indicator quantity, (Avg) is the average value of the amplitude of the signal shown in FIG. 4. A second flow indicator quantity is the standard deviation of the signal (StDev) which reflects the harmonic power of the signal and is an important variable for any irregularly varying signal that carries significant information. A third flow indicator quantity is the characteristic auto-correlation time (Auto). This is the time scale during which the signal loses linear correlation and is a measure of the rate of mixing in a process. The auto-correlation quantity is the integral over all time of the signal multiplied times a timed delayed version of the signal. For long time delays, the auto-correlation approaches $$n\overline{x}^2 \qquad (1)$$

where n is the number of readings in the record. For no time delay, the auto-correlation equals:

$$\Sigma x^2 \qquad (2)$$

measured in sampling intervals, the auto-correlation quantity is:

$$\delta t_{auto} = \frac{\Sigma x^2 - \bar{n}x^2}{\Sigma x^2 - \Sigma x_i x_{i+1}} \quad (3)$$

A fourth flow indicator quantity is the average difference, more specifically the average absolute value difference in sequential readings. This flow indicator quantity provides a first order indication of how rapidly the data change on the smallest time scale.

A fifth flow indicator quantity is the root mean square difference (RMSDif) in sequential readings, a measure similar to the average difference, but tends to weigh larger changes in the sequential readings more strongly than smaller changes.

Another flow indicator quantity is the period of average crossing waves variable, (APd), which is reflective of the average number of readings that occur between upward crossings of the average value of the amplitude as shown at 60, FIG. 6, and characterized as the time length of first order signal variations.

Another flow indicator quantity, (ARMSPd), is the root mean square value of the period of average crossing waves variable which emphasizes longer-period waves. A related flow indicator quantity, (ADur), is the duration of average crossing waves which is a measure of the average number of readings that occur between an upward and downward crossing of the average amplitude value as shown at 60, FIG. 6. A related flow indicator quantity is the root mean square value of the duration of average crossing waves, (ARMSDur).

The period of standard deviation crossing waves flow indicator quantity, (sPd), represented in FIG. 7, is a measure similar to the average period of average crossing waves, but in this case the bar is raised somewhat to look at the period of waves that cross the average plus the standard deviation as shown at 70, FIG. 7. A related flow indicator quantity is the root mean square value of the period of standard deviation crossing waves value, (sRMSPd). Another flow indicator quantity, (sDur), is the duration of standard deviation crossing waves as shown in 72, FIG. 7. Finally, a related flow indicator quantity is the root mean square duration of standard deviation crossing waves, (sRMSDur). Other flow indicator quantities, however, are within the scope of this invention.

One version of a Quick Basic 4.5 programming language program running under the DOS operating system, operating on computer sub-system 28, FIG. 1, for calculating the above flow indicator quantities is included herein as follows:

```
' Program FLOWINDI: accepts command line input of a DataFile$ name or the
' name of a file containing a list of data files (FileList$). It opens
' each DataFile$, and calculates flow indicator quantities. The results
' are placed in an output file named using the input file name plus the
' extension ".OUT". For a FileList$ input file, the output file contains
' one line for each input file named in the list.

' Usage:
'
'           FLOWINDI.EXE [DataFile$] [-L FileList$]

' Without arguments, program provides a description of usage syntax.
' With DataFile$ provided, program analyzes the single file and puts results
'     in a new file named the same as DataFile$ but with the extension .OUT.
' With -L FileList$ provided, program analyzes each file listed in FileList$
'     and puts results in a new file with the same name as FileList$ but with
'     the extension .OUT.

' Metacommand that uses maximum available conventional memory.
  $DYNAMIC

' Default variable type is integer in this module.
  DEFINT A-Z

' Declare the Comline subprogram (which retrieves the program command line),
' as well as the number and type of its parameters. This subprogram is
' provided with QuickBasic 4.5 as an example program.
  DECLARE SUB Comline (N, a$(), Max)

' Dimension arrays
  DIM a$(1 TO 15)     ' Contains the command line parameters
  DIM f$(1 TO 100)    ' Contains list of input files
  DIM array(-30000 TO 30000)    ' Contains array of integer readings, good for
                                ' 2 seconds of data at 30kHz.

' Get what was typed on the command line.
  CALL Comline(N, a$(), 6)

' Figure out whether command line is workable:

IF N = 0 GOTO Bomb    ' No command line arguments
  IF N > 2 GOTO Bomb    ' Too many arguments
  IF N = 2 AND (a$(1) <> "-L" AND a$(1) <> "-l") GOTO Bomb   ' Wrong syntax for
            ' FileList$ operation GOTO NoBomb  ' No problems so far...

Bomb:   ' Give user program usage syntax pointers, then quit.
        PRINT "
        PRINT "         FLOWINDI:  Calculates signature quantities for 1 or more
        PRINT "                    input data files.
        PRINT "
        PRINT "         Usage:  FLOWINDI [DataFile] [-L ListFile]
        PRINT "
        PRINT "         1) DataFile - path and name of single input file, must be a
        PRINT "            single column of normal integers (-32768 to +32767).
        PRINT "         2) ListFile - path and name of text file containing a list of
        PRINT "            paths + names of files to be analyzed (single column).
        PRINT "         3) Command line can contain DataFile _OR_ ListFile (not both).
```

```
        PRINT "    4) Results are placed in an output file named using input file "
        PRINT "       name with extension replaced by .OUT.                       "
        PRINT "                                                                   "

END

NoBomb: ' OK, so far so good. Next, open the input list file (if there
        ' is one) and create an output file.

IF N = 1 THEN    ' Only one input file.
    f$(1) = a$(1)
    iFiles = 1

ELSE             ' N=2, FileList$ input, get list of files

FileList$ = a$(2)
    ON ERROR GOTO Handle1
        flag = 1
        OPEN FileList$ FOR INPUT AS #1
    ON ERROR GOTO 0 iFiles = 0   ' Number of files in list
    DO WHILE NOT EOF(1) ' Read list of input files
        INPUT #1, f$(iFiles + 1)
        iFiles = iFiles + 1
    LOOP
    CLOSE #1     ' Done with FileList$
    flag = 2
    IF iFiles = 0 THEN GOTO Handle1 ' No file names
END IF 'Next, create output file with name based on FileList$ or DataFile$, as
' appropriate.

IF N = 1 THEN
        file$ = a$(1)
    ELSE
        file$ = FileList$
    END IF ' Find extension in file name
    FOR ichar = 1 TO LEN(file$)
        IF MID$(file$, ichar, 1) = "." THEN
            ' everything to the right of this character must be extension
            oFile$ = LEFT$(file$, ichar) + "OUT"
        END IF
    NEXT ichar ' Plug hole for case where file didn't have an extension initially
IF RIGHT$(oFile$, 4) <> ".OUT" THEN oFile$ = oFile$ + ".OUT"

' Open output file
    ON ERROR GOTO Handle1
        flag = 3
        OPEN oFile$ FOR OUTPUT AS #2
    ON ERROR GOTO 0

' Write header line in output file
    PRINT #2, "  FileName     Average    StDev     Auto      AvgDif    RMSDif  ";
    PRINT #2, "              APd        ARMSPd    ADur      ARMSDur   SPd       SRMSPd  ";
```

```
        PRINT #2, "   SDur    SRMSDur "

' Next, analyze each input file in turn and print results in oFile$.

FOR fileNum = 1 TO iFiles    ' For each data file
    ON ERROR GOTO Handle2    ' Data file open error
        OPEN f$(fileNum) FOR INPUT AS #1
    ON ERROR GOTO 0
    PRINT "Analyzing "; f$(fileNum); "."

' First, go through data set to input data array and calculate preliminary
' flow indicators.

J& = 0           ' Number of values found in file (so far)
Sum& = 0         ' Accumulator of sum of raw values
Sum2# = 0        ' Accumulator of sum of values squared
SumDif# = 0      ' Accumulator for sum of absolute value changes in seq rdgs.
SumDif2# = 0     ' Accumulator for sum of squares of differences in seq rdgs.
Corr# = 0        ' Accumulator for product of current value and preceding value.
DO WHILE NOT EOF(1)
    INPUT #1, array(J& + 1 - 30000)
    J& = J& + 1
    IF J& > 1 THEN  'Not first data point
        SumDif# = SumDif# + ABS(value - oldvalue&)
        SumDif2# = SumDif2# + (value - oldvalue&) ^ 2
        Corr# = Corr# + value * oldvalue&
    END IF
    Sum& = Sum& + value
    Sum2# = Sum2# + value ^ 2
    oldvalue& = value
LOOP CLOSE #1    ' Done with raw data, so close file.

PRINT "There are "; J&; " points in the data set."

'Calculate a few results
Ave! = Sum& / J&       ' Average value
SDev! = SQR(Sum2# / J& - Ave! ^ 2)    ' Standard deviation
Auto! = (Sum2# - J& * Ave! ^ 2) / (Sum2# - Corr#)   ' Characteristic
                                                    ' autocorrelation time
AvgDif! = SumDif# / (J& - 1)  ' Average absolute value change in seq readings
RmsDif! = SQR(SumDif2# / (J& - 1))  ' RMS change in sequential readings ' Next go through the data array a couple of times.

' Find and characterize large events (crossings of average and
'  avg+(std-dev) lines).

' Note: the following is not the most efficient method of performing this
'  analysis, but is logically simple and easier to read (and debug). A final
'  version could be performed in half as many operations.

' Crossings of the average value line:

' First, find the first positive crossing of average line:

X = 1
```

```
Y = 0
DO UNTIL Y = 1
    IF array(X + 1 - 30000) > Ave! AND array(X - 30000) < Ave! THEN Y = 1
    X = X + 1
LOOP 'Resulting X is the first positive crossing of the average line ' Next, start there and find number of positive crossings and duration of
' periods above average and periods between positive crossings aNum = 0            ' No +ve avg crossings counted yet
avgCross = X        ' Pointer to most recent +ve crossing of avg
ADur = 0            ' Accumulator for duration above avg
aDur2& = 0          ' Accumulator for duration squared above avg
aPd2& = 0           ' Accumulator for square-length of crossing period
FOR ptNum = X + 1 TO NArray
    IF array(ptNum - 30000) > Ave! AND array(ptNum - 1 - 30000) < Ave! THEN
        ' +ve crossing
        aNum = aNum + 1    'Count the crossing
        aPd2& = aPd2& + (ptNum - avgCross) ^ 2 'Accumulate square period
        avgCross = ptNum   'Update pointer to +ve crossing
    END IF
    IF array(ptNum - 30000) < Ave! AND array(ptNum - 1 - 30000) > Ave! THEN
        ' -ve crossing
        ADur = ADur + ptNum - avgCross   ' Accumulate duration above bar
        aDur2& = aDur2& + (ptNum - avgCross) ^ 2   ' Accum dur^2 above bar
        lastMinus = ptNum    'Store pointer to -ve crossing
    END IF
NEXT ptNum ' Calculate statistics for average-crossing events APd! = (lastMinus - X) / aNum       ' Avg period of average-crossing events
ARmsPd! = SQR(aPd2& / aNum)         ' RMS -----------------'-----------------
ADur! = ADur / aNum                 ' Avg duration of time above avg
ARmsDur! = SQR(aDur2& / aNum)       ' RMS -----------'---------------

' Next, look for crossings of the average+(standard deviation) line:

' First, find the first positive crossing of avg+(std-dev) line:

X = 1
Y = 0
bar! = Ave! + SDev!
DO UNTIL Y = 1
    IF array(X + 1 - 30000) > bar! AND array(X - 30000) < bar! THEN Y = 1
    X = X + 1
LOOP 'Resulting X is the first positive crossing of the avg+(std-dev) line ' Next, start there and find number of positive crossings and duration of
' periods above the bar and periods between positive crossings aNum = 0            ' No +ve avg+(std-dev) crossings counted yet
avgCross = X        ' Pointer to most recent +ve crossing of avg+(std-dev)
ADur = 0            ' Accumulator for duration above avg+(std-dev)
```

```
aDur2& = 0          ' Accumulator for duration squared above avg+(std-dev)
aPd2& = 0           ' Accumulator for square-length of crossing period
FOR ptNum = X + 1 TO NArray
    IF array(ptNum - 30000) > bar! AND array(ptNum - 1 - 30000) < bar! THEN
        ' +ve crossing
        aNum = aNum + 1  'Count the crossing
        aPd2& = aPd2& + (ptNum - avgCross) ^ 2  'Accumulate square period
        avgCross = ptNum    'Update pointer to +ve crossing
    END IF
    IF array(ptNum - 30000) < bar! AND array(ptNum - 1 - 30000) > bar! THEN
        ' -ve crossing
        ADur = ADur + ptNum - avgCross   ' Accumulate duration above bar
        aDur2& = aDur2& + (ptNum - avgCross) ^ 2    ' Accum dur^2 above bar
        lastMinus = ptNum   'Store pointer to -ve crossing
    END IF
NEXT ptNum ' Calculate statistics for avg+(std-dev) crossing events SPd! = (lastMinus - X) / aNum       'Avg period of events above avg+(std-dev)
SRmsPd! = SQR(aPd2& / aNum)         'RMS -----------"-------------------
SDur! = ADur / aNum                 'Avg duration of time above bar
SRmsDur! = SQR(aDur2& / aNum)       'RMS -----------"-------------------

' Print results in output file:

' First, find 8.3 format name of input file (i.e., strip off path)

fileName$ = ""      ' Preset to null in case path isn't present
FOR i = 1 TO LEN(f$(fileNum))
    IF MID$(f$(fileNum), LEN(f$(fileNum)) + 1 - i, 1) = "\" THEN
        fileName$ = RIGHT$(f$(fileNum), i - 1)
        EXIT FOR
    END IF
NEXT i IF fileName$ = "" THEN fileName$ = f$(fileNum)   ' No path SELECT CASE LEN(fileName$):
CASE 12:        ' Sheesh, what we won't do for a clean output format!
    PRINT #2, fileName$;
CASE 11:
    PRINT #2, " "; fileName$;
CASE 10:
    PRINT #2, "  "; fileName$;
CASE 9:
    PRINT #2, "   "; fileName$;
CASE 8:
    PRINT #2, "    "; fileName$;
CASE 7:
    PRINT #2, "     "; fileName$;
CASE 6:
    PRINT #2, "      "; fileName$;
CASE 5:
    PRINT #2, "       "; fileName$;
CASE 4:
    PRINT #2, "        "; fileName$;
CASE 3:
    PRINT #2, "         "; fileName$;
```

```
CASE 2:
PRINT #2, "          "; fileName$;
CASE 1:
PRINT #2, "          "; fileName$;
END SELECT PRINT #2, USING "####.##"; Ave!;
PRINT #2, " ";
PRINT #2, USING "####.##"; SDev!;
PRINT #2, " ";
PRINT #2, USING "####.##"; Auto!;
PRINT #2, " ";
PRINT #2, USING "####.##"; AvgDif!;
PRINT #2, " ";
PRINT #2, USING "####.##"; RmsDif!;
PRINT #2, " ";
PRINT #2, USING "####.##"; APd!;
PRINT #2, " ";
PRINT #2, USING "####.##"; ARmsPd!;
PRINT #2, " ";
PRINT #2, USING "####.##"; ADur!;
PRINT #2, " ";
PRINT #2, USING "####.##"; ARmsDur!;
PRINT #2, " ";
PRINT #2, USING "####.##"; SPd!;
PRINT #2, " ";
PRINT #2, USING "####.##"; SRmsPd!;
PRINT #2, " ";
PRINT #2, USING "####.##"; SDur!;
PRINT #2, " ";
PRINT #2, USING "####.##"; SRmsDur!

Restart:    'Re-entry point for missing input file

NEXT fileNum

CLOSE #2

END

Handle1:    ' Fatal errors that require program termination:
            PRINT
            IF flag = 1 THEN PRINT "Couldn't open list file "; FileList$; " for in
            IF flag = 2 THEN PRINT "No file names in "; FileList$; "."
            IF flag = 3 THEN PRINT "Couldn't open "; oFiles; " for output."
            PRINT
            END Handle2:    ' Non-fatal errors that allow program to continue:
            PRINT
            PRINT "Can't open file "; f$; " for input."
            ON ERROR GOTO 0
            GOTO Restart DEFINT A-Z
SUB Comline (NumArgs, Args$(), MaxArgs) STATIC
CONST TRUE = -1, FALSE = 0

NumArgs = 0: in = FALSE
```

```
' Get the command line using the COMMAND$ function.
    C1$ = COMMAND$
    L = LEN(C1$)
' Go through the command line a character at a time.
    FOR i = 1 TO L
        C$ = MID$(C1$, i, 1)
        'Test for character being a blank or a tab.
        IF (C$ <> " " AND C$ <> CHR$(9)) THEN
' Neither blank nor tab.
' Test to see if you're already
' inside an argument.
            IF NOT in THEN
' You've found the start of a new argument.
' Test for too many arguments.
                IF NumArgs = MaxArgs THEN EXIT FOR
                NumArgs = NumArgs + 1
                in = TRUE
            END IF
' Add the character to the current argument.
            Args$(NumArgs) = Args$(NumArgs) + C$
        ELSE
' Found a blank or a tab.
' Set "Not in an argument" flag to FALSE.
            in = FALSE
        END IF
    NEXT i

END SUB
```

This program accepts a command line of the form: NAS96072 [DataFile$][-1 FileList$]. If the analysis of a single data file is of interest, then the DataFile$ field above is filled with the path and name of the file containing the data. If a list of files are to be analyzed, then the -1 switch is used and the path of the name of an ASCII file containing a list of the files used as the FileList$ variable. In either event, single ASCII output files are created from the DataFile$ or ListFile$ name, with the file name extension replaced with "OUT". This file contains one row that is a header describing the names of each of the signature quantities that was calculated, plus one row for each data file that was analyzed containing the values of the corresponding signature quantities.

Figure 8:
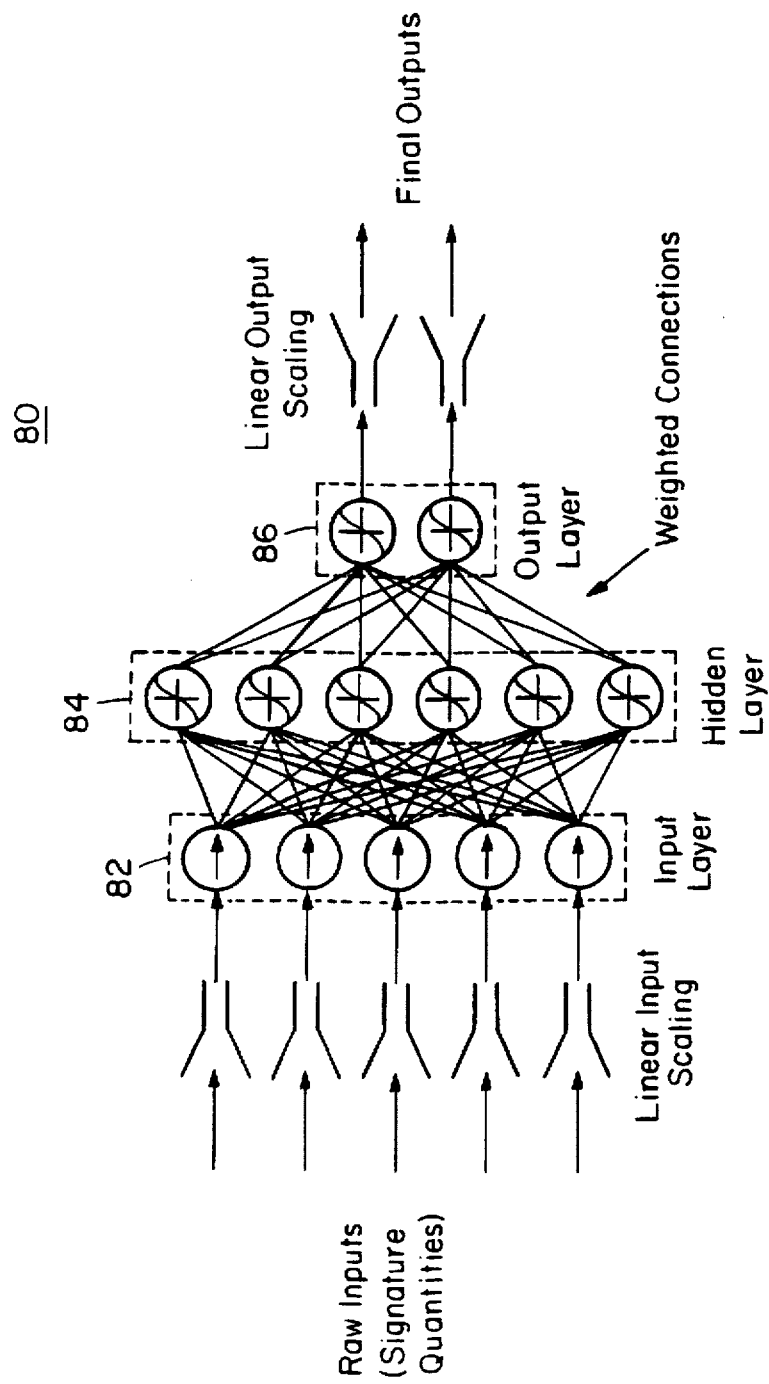
FIG. 8 is a schematic view of a neural network used to determine the flow rate of a flow in accordance with the subject invention.

Neural network 80, FIG. 8, is then used to determine the flow rate and other typical variables associated with single and two phase flows in conduit 14, FIG. 1. The primary reason neural network 80 is used is that it has the ability to handle arbitrarily non-linear correlations involving abrupt transitions, strongly varying behaviors, or complicated interactions among input variables. In addition, neural network 80 does not require any assumptions about the form or the correlation between a set of inputs and the desired set of outputs. Neural network 80 is programmed by training a set of weighted connections, rather than by explicitly defining a set of operations that must be performed. Once trained, neural network 80 is then implemented in a very fast, efficient software, firmware, or hardware environment rendering it ideally suited for real time applications. In addition, once properly trained, neural network 80 is extraordinarily fault tolerant, and/or fault indicating. Thus, if the data is noisy or occasionally erroneous or missing, a neural network can indicate this and still provide a reasonable estimate of the operating conditions.

In practice, neural network 80 is trained by first inputting known flow indicator quantities for a broad range of known conditions and training the network to handle those particular cases. Once network 80 is trained, it can be applied to a new set of flow indicator quantities providing a means of analyzing data in a real world applications.

Neural network 80 is best viewed as being made up of a layer of neurons. The most common type of a neural network, called a "back propagation" network, contains three layers: input layer 82, hidden layer 84, and output layer 86. The input layer receives the input information, in this case the flow indicator quantities discussed above. Each of the inputs is scaled from its full range to a range of (-1, 1.) which the network is very good at handling. No processing is done at the input layer, instead each neuron simply passes along its input value which is fed to the next layer through a set of weighted connections.

Usually, successive layers are thoroughly interconnected so the weighted connections link each neuron in the input layer to each neuron in the hidden layer. The value that reaches a hidden neuron along a given connection is the product of the value injected into the connection by the input neuron and the value of the connection weight. In hidden layer 84, each neuron sums the values that reach it via the connections and then applies a simple, non-linear transformation to that value. Gaussian (bell-shaped) and sigmoidal (S-shaped) functions are the most commonly used partly because they easily calculate.

In a preferred embodiment, neural network 80 uses a sigmoidal function called a "logistic" function. This function maps any input value in an infinite range to an output of (-1, 1). The resulting value is then fed forward along the weighted connections to output layer 86. Output layer 86 functions identically to the hidden layer, summing the weighted values that are presented to it, applying a logistic transformation, and outputting the result. The output value in the range (-1,1) is scaled back to the full range of interest, producing a final result of the network.

In the subject invention, the eighteen flow indicator quantity inputs were used for each data set and one or two outputs corresponding to the flow rates or yes/no answers. The number of hidden neurons can vary considerably, depending upon the difficulty of the required calculation. More neurons permit greater complexity, but slow the processing speed. The "NeuroShell 2" neural network simulation program available from Ward Systems Group may be used to implement neural network 80, FIG. 8.

Training back propagation network 80, requires the preparation of a set of training data sets containing both the inputs and the desired outputs. The weighting values initially are selected at random. During training, training cases are chosen at random, presented to the network, and the error in the network's output is "back propagated" through the network to determine minimum changes to the weighted values that will eliminate the error. By performing this process over and over, updating the weighted values as needed, the network's calculational accuracy continually improves until, finally, it is not improved further. If the network's accuracy is acceptable at that point, it can be used as desired to rapidly produce an output value for the set of input values.

Neural network 80 may be subject to "over-training" unless care is taken to train it properly. Over-training is the ability of the network to recognize individual training sets, rather than the basic variation in the patterns between different training sets. Over-trained networks often perform poorly when used to estimate the state of new input sets. This problem can be avoided by using one sub-set of the available data sets as training data, and the remainder as test data. The network is trained using the training sets, but a new set of values for the connection weights is saved only when it performs better with the test data (which were not used to train the network). This method usually results in a network with a satisfactory ability to "generalize" beyond the training data to the larger range of possible inputs.

Each data file of raw data is filtered to a signature file using the computer program described above. These signature files are merged with a master spreadsheet that contained the pressure, temperature, and flow rate information for each test. From this master spreadsheet, the appropriate information with respect to the phase content (liquid/two-phase), flow (flow/no-flow) and flow indicator quantities are input to neural network 80 for processing.

To train neural network 80, the water flow of a two phase water/air flow is determined using an electric digital flow meter such as a Great Plains (Wichita, Kans.) 0.3–3 gpm and/or 3 gpm–50 gpm capacity meter. Air flow is measured using either or both of two mass flow meters from Omega Engineering (Stamford, Conn.) with flow ranges of 0–50 standard liters/minutes of nitrogen.

For air-water flows, the following parameters are of primary interest: whether there is a flow in the pipe, whether there is air in the flow, if the flow is pure liquid, the flow rate: If the flow is two-phase, the water and air flow rates are also of primary interest. Eighty-two test sets are selected at random as test sets, leaving 121 sets that may be used for training the network. Whether there is flow in the pipe and whether there is air in the flow are both simple yes/no answers. So, a value of 1 is set to the desired output for a true answer and 0 for a false answer. In actuality, any value greater than 0.5 for a true answer or less than 0.5 for a false answer is effectively as good.

Once neural network 80 is trained in accordance with this invention, it will predict the existence of a flow and whether there was presence of air in the flow.

Another neural network may then be trained, for pure liquid flows, to determine the water flow rate.

Another neural network may be trained in accordance with this invention to determine the water and air flow rates of a two-phase flow.

Thus, the subject invention reduces the sampling rate required by generating an amplitude envelope of the sensor signal thus eliminating the need for complicated hardware and software. And, the subject invention eliminates the need to use invasive sensors which often fail to work properly at low or high temperatures and in harsh or adverse conditions.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A flow analysis system comprising:
    a sensor in communication with a conduit including a flow therein for transmitting a signal which varies depending on the characteristics of the flow in the conduit;
    a filter, responsive to said signal, tuned to pass a narrow band of frequencies proximate the resonant frequency of the sensor;
    means for generating an amplitude envelope of the filtered signal;
    means, responsive to the amplitude envelope, for calculating a plurality of flow indicator quantities representative of the flow in the conduit; and
    means, responsive to the flow indicator quantities, for determining the flow rate of the flow in the conduit.

2. The system of claim 1 in which said means for calculating includes means for sampling the amplitude envelope at a rate less than or equal to the resonant frequency of the sensor.

3. The system of claim 1 in which said means for determining includes a neural network trained to calculate the flow rate in accordance with a plurality of flow indicator quantities representative of a known flow rate in the conduit.

4. The system of claim 1 in which said means for calculating includes means for determining variations in the amplitude of the amplitude envelope.

5. The system of claim 4 in which a said flow indicator quantity includes the average value of the amplitude.

6. The system of claim 4 in which a said flow indicator quantity includes the standard deviation of the amplitude.

7. The system of claim 4 in which a said flow indicator quantity includes the characteristic auto-correlation time.

8. The system of claim 4 in which a said flow indicator quantity includes the average absolute value difference of the amplitude.

9. The system of claim 4 in which a said flow indicator quantity includes the average crossing waves variable.

10. The system of claim 9 in which a said flow indicator quantity includes the root mean square difference of the average crossing waves variable.

11. The system of claim 9 in which a said flow indicator quantity includes the duration of the average crossing waves variable.

12. The system of claim 9 in which a said flow indicator quantity includes the root mean square value of the duration of average crossing waves variable.

13. The system of claim 4 in which a said flow indicator quantity includes the period of standard deviation crossing waves.

14. The system of claim 13 in which a said flow indicator quantity includes duration of crossing waves.

15. The system of claim 4 in which a said flow indicator quantity includes the root mean square duration of standard deviation crossing waves.

16. The system of claim 4 in which a said flow indicator quantity includes both the average value of the amplitude of the envelope and the standard deviation of the average value of the amplitude of the envelope.

17. A flow analysis system comprising:
    an acoustic sensor in communication with a conduit including a flow therein for transmitting a signal which varies depending on the characteristics of the flow in the conduit;
    means, responsive to the amplitude envelope, for calculating a plurality of flow indicator quantities representative of the flow in the conduit; and
    means, responsive to the flow indicator quantities, for determining the flow rate of the flow in the conduit.

18. The system of claim 17 further including an amplifier for amplifying said signal.

19. The system of claim 17 further including a filter, tuned to pass a narrow band of frequencies proximate the resonant frequency of the sensor.

20. The system of claim 17 further including means for generating an amplitude envelope of the filtered signal.

21. The system of claim 20 further including means for sampling said amplitude envelope at a rate less than or equal to the frequency of the signal transmitted by the sensor.

22. A flow analysis system comprising:
    an acoustic sensor in communication with a conduit including a flow therein for transmitting a signal which varies depending on the characteristics of the flow in the conduit;
    means for amplifying the signal;
    a filter, responsive to the amplified signal and tuned to pass a narrow band of frequencies the proximate resonant frequency of the acoustic sensor;
    means for generating an amplitude envelope of the filtered signal;
    means, responsive to the amplitude envelope, for calculating a plurality of flow indicator quantities representative of the flow in the conduit; and
    means, responsive to the flow indicator quantities, for determining the flow rate of the flow in the conduit.

23. The system of claim 22 in which said means for calculating includes means for sampling the amplitude envelope at a rate less than or equal to the resonant frequency of the sensor.

24. The system of claim 22 in which said means for determining includes a neural network trained to calculate the flow rate in accordance with a plurality of flow indicator quantities representative of a known flow rate in the conduit.

25. The system of claim 22 in which said means for calculating includes means for determining variations in the amplitude of the amplitude envelope.

26. A flow analysis method comprising:
    coupling a sensor to a conduit with a flow therein and transmitting a signal which varies depending on the characteristics of the flow in the conduit;

using a filter, responsive to the signal and tuned to pass a narrow band of frequencies proximate the resonant frequency of the sensor;

generating an amplitude envelope of the filtered signal;

calculating, in response to the amplitude envelope, a plurality of flow indicator quantities representative of the flow in the conduit; and in response to the flow indicator quantities, determining the flow rate of the flow in the conduit.

27. The method of claim 26 in which calculating includes sampling the amplitude envelope at a rate less than or equal to the resonant frequency of the sensor.

28. The method of claim 26 in which determining includes using a neural network trained to calculate the flow rate in accordance with a plurality of flow indicator quantities representative of a known flow rate in the conduit.

29. The method of claim 26 in which calculating includes determining variations in the amplitude of the amplitude envelope.

30. The method of claim 29 in which a said flow indicator quantity includes the average value of the amplitude.

31. The method of claim 29 in which a said flow indicator quantity includes the standard deviation of the amplitude.

32. The method of claim 29 in which a said flow indicator quantity includes the characteristic auto-correlation time.

33. The method of claim 29 in which a said flow indicator quantity includes the average absolute value difference of the amplitude.

34. The method of claim 29 in which a said flow indicator quantity includes the average crossing waves variable.

35. The method of claim 29 in which a said flow indicator quantity includes the root mean square difference of the average crossing waves variable.

36. The method of claim 29 in which a said flow indicator quantity includes the duration of the average crossing waves variable.

37. The method of claim 29 in which a said flow indicator quantity includes the root mean square value of the duration of average crossing waves variable.

38. The method of claim 29 in which a said flow indicator quantity includes the period of standard deviation crossings.

39. The method of claim 29 in which a said flow indicator quantity includes the duration of crossing waves.

40. The method of claim 29 in which a said flow indicator quantity includes the root mean square duration of standard deviation crossing waves.

41. The method of claim 29 in which a said flow indicator quantity includes both the average value of the amplitude of the envelope and the standard deviation of the average value of the amplitude of the envelope.

42. A flow analysis method comprising:

coupling an acoustic sensor to a conduit with a flow therein and transmitting a signal which varies depending on the characteristics of the flow in the conduit;

using a filter, responsive to the signal and tuned to pass a narrow band of frequencies proximate the resonant frequency of the acoustic sensor;

generating an amplitude envelope of the filtered signal;

calculating a plurality of flow indicator quantities representative of the flow in the conduit from the amplitude envelope; and in response to the flow indicator quantities, determining the flow rate of the flow in the conduit.

43. The method of claim 42 in which calculating includes sampling the amplitude envelope at a rate less than or equal to the resonant frequency of the sensor.

44. The method of claim 42 in which determining includes using a neural network trained to calculate the flow rate in accordance with a plurality of flow indicator quantities representative of a known flow rate in the conduit.

45. The method of claim 42 in which calculating includes determining variations in the amplitude of the amplitude envelope.

46. A flow analysis method comprising:

coupling an acoustic sensor to a conduit with a flow therein and transmitting a signal which varies depending on the characteristics of the flow in the conduit;

using the amplitude envelope to calculate a plurality of flow indicator quantities representative of the flow in the conduit; and determining the flow rate of the flow in the conduit from the flow indicator quantities.

47. The method of claim 46 further including amplifying the acoustic sensor signal.

48. The method of claim 46 further including using a filter, tuned to pass frequencies proximate the resonant frequency of the acoustic sensor.

49. The method of claim 46 further including generating an amplitude envelope of the acoustic sensor signal.

50. The method of claim 49 further including sampling the amplitude envelope at a rate less than or equal to the resonant frequency of the acoustic sensor.

* * * * *